(12) United States Patent
Birnkrant et al.

(10) Patent No.: US 11,213,192 B2
(45) Date of Patent: Jan. 4, 2022

(54) ENDOSCOPE DEVICE AND METHOD WITH ILLUMINATION FIBER BUNDLES HAVING MULTIPLE NUMERICAL APERTURES

(71) Applicant: KARL STORZ Endovision, Inc., Charlton, MA (US)

(72) Inventors: Dashiell Birnkrant, Sutton, MA (US); Robert Tremblay, Framingham, MA (US)

(73) Assignee: KARL STORZ Endovision, Inc., Charlton, MA (US)

( * ) Notice: Subject to any disclaimer, the term of this patent is extended or adjusted under 35 U.S.C. 154(b) by 129 days.

(21) Appl. No.: 16/678,376

(22) Filed: Nov. 8, 2019

(65) Prior Publication Data

US 2021/0137374 A1    May 13, 2021

(51) Int. Cl.
*A61B 1/06*     (2006.01)
*A61B 1/05*     (2006.01)
*A61B 1/00*     (2006.01)
*A61B 1/267*    (2006.01)

(52) U.S. Cl.
CPC ........ *A61B 1/0684* (2013.01); *A61B 1/00167* (2013.01); *A61B 1/00174* (2013.01); *A61B 1/051* (2013.01); *A61B 1/0676* (2013.01); *A61B 1/267* (2013.01)

(58) Field of Classification Search
CPC ... A61B 1/0684; A61B 1/00174; A61B 1/267; A61B 1/051; A61B 1/00167; A61B 1/0676; A61B 1/07; G02B 23/2469
See application file for complete search history.

(56) References Cited

U.S. PATENT DOCUMENTS

| | | | |
|---|---|---|---|
| 4,641,912 A * | 2/1987 | Goldenberg | A61B 18/245 385/117 |
| 8,657,738 B2 | 2/2014 | Kitano | |
| 8,948,560 B1 * | 2/2015 | Wach | A61B 1/07 385/125 |
| 2019/0223706 A1 * | 7/2019 | Takeuchi | A61B 1/00096 |

FOREIGN PATENT DOCUMENTS

JP    9066020 A    3/1997

* cited by examiner

*Primary Examiner* — Aaron B Fairchild
(74) *Attorney, Agent, or Firm* — Michael J. Loi; David Noel Villalpando

(57) ABSTRACT

An optical scope includes a body and an elongated shaft. The shaft distal end holds an optical assembly including an imaging lens with a field of view of at least 90 degrees. An LED is coupled to the body and has an output numerical aperture (NA) providing a critical angle larger than the field of view. A first pair of fiber bundles have proximal ends receiving light from the LED with distal ends presented at the shaft distal face, and an NA providing a critical angle less than the field of view. A second pair of fiber bundles also receive light from the LED with distal ends having at the shaft distal face, and have an NA providing a critical angle at least as large as the field of view. The bundles are positioned around imaging lens such that they create a light having a desired intensity profile and properties.

16 Claims, 5 Drawing Sheets

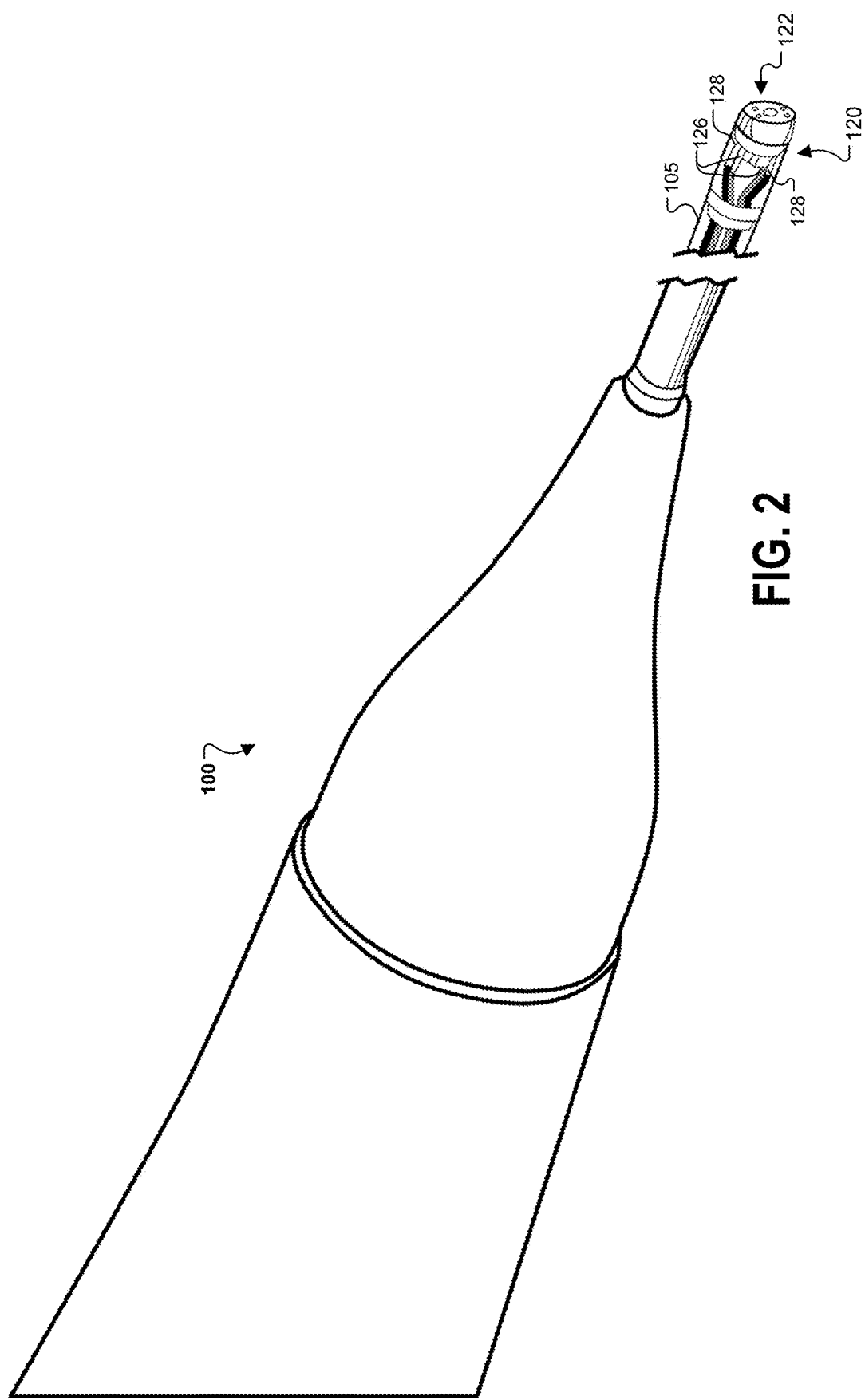

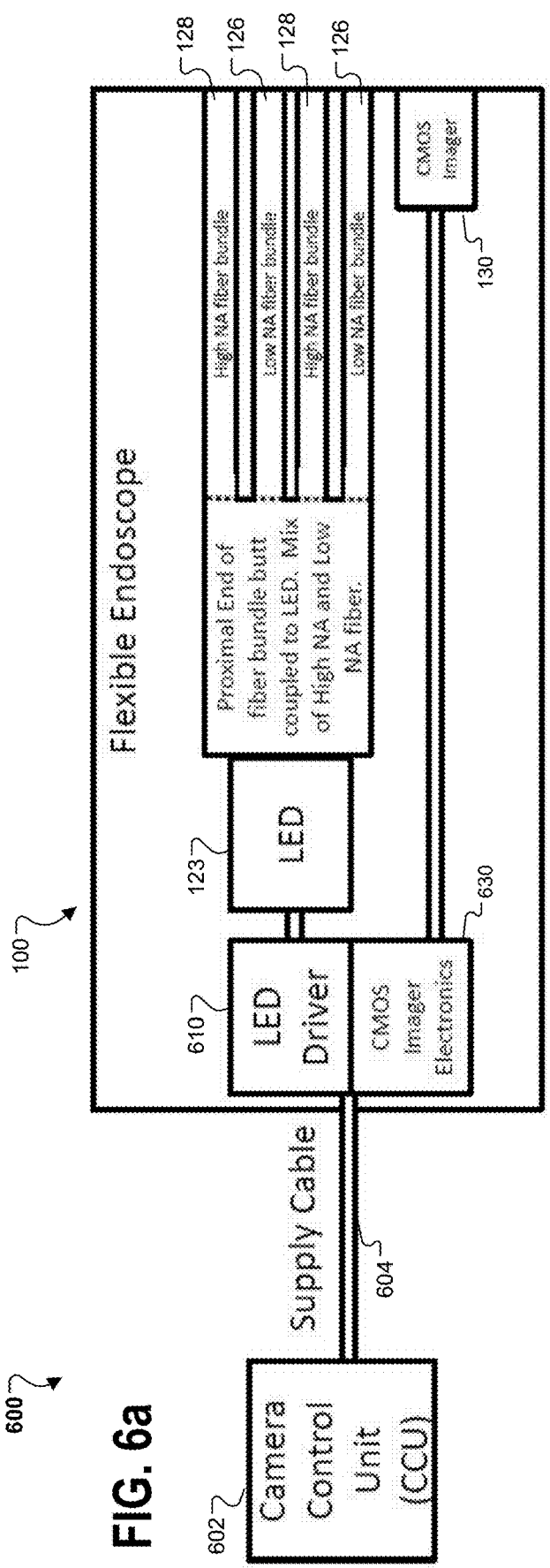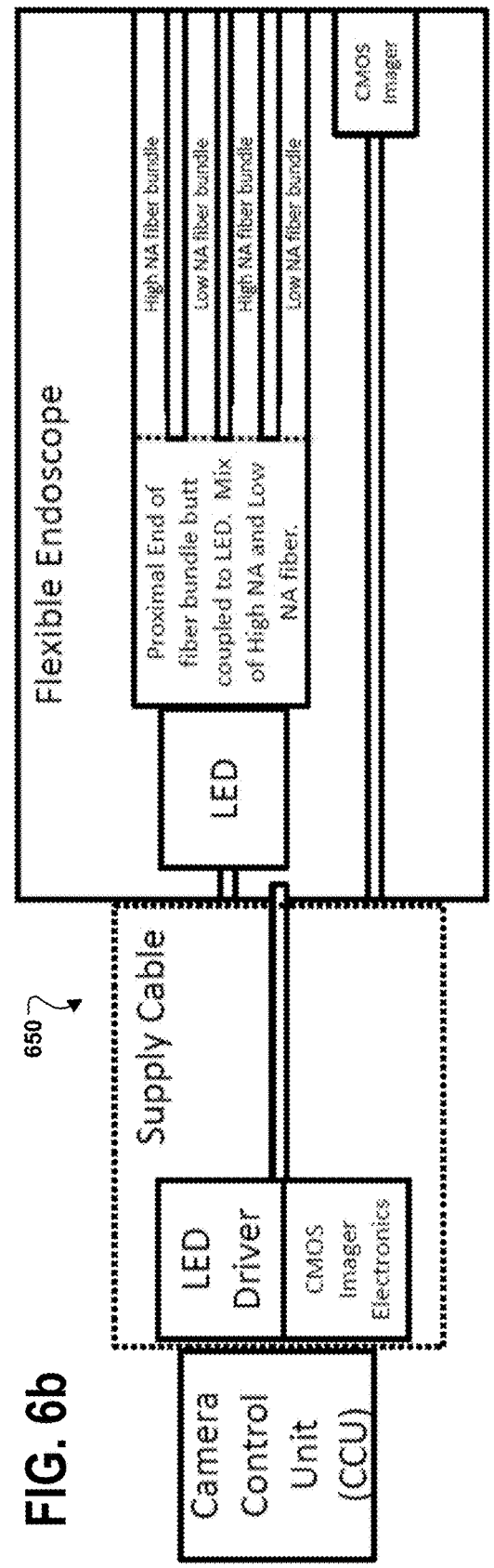
FIG. 6a
FIG. 6b

ENDOSCOPE DEVICE AND METHOD WITH ILLUMINATION FIBER BUNDLES HAVING MULTIPLE NUMERICAL APERTURES

TECHNICAL FIELD OF THE INVENTION

The invention relates generally to the field of medical image capture and more specifically to wide-angle endoscopes having fiber bundles carrying light to a distal tip.

BACKGROUND OF THE INVENTION

Rhino laryngoscopes are used for examination of the nose and larynx. Many modern rhino laryngoscopes include a flexible shaft with an electronic image sensor positioned to acquire images or video from the perspective of the distal end of the flexible shaft. The shaft often includes an illumination source at the distal end, which may be a fiber optic bundle carrying light from the scope body, or an LED positioned at the shaft distal end.

The illumination source of current flexible rhino-laryngoscopes are typically made up of a bundle of only high numerical aperture (NA) illumination fiber, which can receive and emit light at high angles with respect to the fiber ends. In practice, the large illumination angle results in a large amount of the emitted light reflecting off of the walls of the nasal cavity near the shaft distal end. This localized effect causes a high return of illumination into the imaging system from these areas and can limit how wide the field of view of the imager can be. If the field of view is too large, the high angle illumination will saturate the image at the edge of the field and make the center of the imager (the depth of the nasal cavity) too dark to see. However, having a large field of view can be advantageous because the user can see more of the nasal cavity walls during the procedure.

What is needed are devices and methods to improve the illumination and field of view of rhino-laryngoscopes providing both the ability to image the cavity walls near the tip of the instrument as well as providing adequate illumination for imaging down the nasal cavity.

SUMMARY OF THE INVENTION

It is an object of the invention to provide improved endoscopic lighting system with a spatially diverse light field having a desired intensity profile with a circumferentially even light intensity within the field of view. It is another object of the invention to enable the use of high intensity illumination in a trench environment such as a laryngoscope application. It is a still further object of the invention to provide such elements in a scope form factor suitable for rhino-laryngoscope applications.

According to a first aspect of the invention, an optical scope includes a body and an elongated shaft. The shaft distal end holds an optical assembly including an imaging lens with a field of view of at least 90 degrees. An LED is coupled to the body and has an output numerical aperture (NA) providing a critical angle larger than the field of view. A first pair of fiber bundles have proximal ends receiving light from the LED with distal ends presented at the shaft distal face, and an NA providing a critical angle less than the field of view. A second pair of fiber bundles also receive light from the LED with distal ends having at the shaft distal face, and have an NA providing a critical angle at least as large as the field of view. The bundles are positioned around imaging lens such that they create a light having a desired intensity profile and properties.

In a first implementation of the first aspect, the distal ends of first and second pairs of fibers are positioned around the imaging lens such that they create a light field with a relatively higher intensity in a central portion, a relatively lower intensity surrounding the central portion, and all the fiber bundles contribute to create a spatially diverse light field with a circumferentially even light intensity within the field of view.

In some implementations of the first aspect, the distal ends of first pair of fiber bundles are positioned opposite each other around the imaging lens.

In some implementations of the first aspect, wherein the field of view is at least 100 degrees, the NA of the first pair of fiber bundles is less than 0.7, and the NA of the second pair of fiber bundles is greater than 0.77. The field of view may be at least 100 degrees, with the NA of the first pair of fiber bundles provided about 0.64, and the NA of the second pair of fiber bundles about 0.86

In some implementations of the first aspect, a plurality of additional fiber bundles are used, with proximal ends receiving light from the LED and distal ends presented at the shaft distal face distributed around the imaging lens, the additional fiber bundles including some with the NA of the first fiber bundle and some with the NA of the second fiber bundle.

In some implementations of the first aspect, the first and second pairs of fiber bundles are butt-coupled to the LED at an LED assembly in the body.

In some implementations of the first aspect, the tip has a horizontal and vertical axis, the shaft distal face is elongated along a vertical axis, and smaller along the horizontal axis, and first pair of fiber bundles are positioned opposite each other above and below the imaging lens and the second pair of fiber bundles are positioned opposite each other above and below the imaging lens, wherein the regions above and below the imaging lens are on the elongated distal face along the vertical axis.

In some implementations of the first aspect, the shaft distal tip is tapered toward the distal face at least on vertical sides of the distal tip.

In some implementations of the first aspect, the shaft distal tip includes an image sensor assembly positioned behind the imaging lens, the image sensor assembly extending further along the horizontal axis than the position of the fiber bundles along the vertical axis.

In some implementations of the first aspect, the optical device is a laryngoscope and the spatially diverse light field has a relative intensity of 80% at about 22 degrees off center, and less than 30% at 40 degrees off center.

In some implementations of the first aspect, a supply cable contains an LED driver connected to the LED, the cable also transmitting collected imaging data to a camera control unit and power from the camera control unit to the optical device.

According to a second aspect of the invention, a system is provided including the optical scope of the first aspect, coupled to a camera control unit operable to receive image data from the optical scope, process the image data, and provide a video output signal to a display for viewing.

According to a third aspect of the invention, method is provided operating an optical scope. The method includes positioning an optical scope in a body cavity with a shaft distal face directed at an area of interest, the optical scope having a field of view of at least 90 degrees. The method includes illuminating at least part of the field of view with first imaging light from two or more illuminating areas, the first imaging light emitted from a first pair of fiber bundles with numerical apertures (NA) providing a critical angle less than the field of view. The field of view is also illuminated with second imaging light from a second two or more illuminating areas, the second imaging light emitted from a second pair of fiber bundles with NAs providing a critical angle at least as great as the field of view. The first and second imaging light combining to create a spatially diverse light field with a circumferentially even light intensity within the field of view.

According to some implementations of the second aspect, the field of view is at least 100 degrees, the NA of the first pair of fiber bundles is less than 0.7, and the NA of the second pair of fiber bundles is greater than 0.85. The NA of the first pair of fiber bundles may be about 0.64, and the NA of the second pair of fiber bundles about 0.86.

According to some implementations of the second aspect, The method further includes emitting one of the first or second image light from each of a plurality of additional fiber bundles with proximal ends receiving light from the LED and distal ends presented at the shaft distal face distributed around the imaging lens, the additional fiber bundles including some with the NA of the first fiber bundle and some with the NA of the second fiber bundle.

According to some implementations of the second aspect, the spatially diverse light field has a relative intensity of 80% at about 22 degrees off center, and less than 30% at 40 degrees off center.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein:

FIG. 2 is a perspective cutaway view of the laryngoscope of FIG. 1;

FIG. 6a is a block diagram of a flexible endoscope according to some embodiments of the invention, and FIG. 6b shows an alternate embodiment wherein the LED driver and CMOS imager electronics are elements of the supply cable;

DETAILED DESCRIPTION OF EXAMPLE EMBODIMENTS

As used herein, first elements (e.g., sensors and lenses) that are "optically arranged" in relation to other elements, refers to the first elements' position along a common optical path that includes first and other elements. For example, a lens group optically arranged between an image sensor and an objective, means that the lens group occupies a portion of the optical path that light travels (e.g., from the objective to the image sensor) for capturing images or video. Directions such as upstream and downstream refer to the direction of light travel.

Because digital cameras, image sensors and related circuitry for signal capture and processing are well-known, the present description will be directed in particular to elements forming part of, or cooperating more directly with, a method and apparatus in accordance with the invention. Elements not specifically shown or described herein are selected from those known in the art. Given the system as shown and described according to the invention in the following materials, software not specifically shown, described or suggested herein that is useful for implementation of the invention is conventional and within the ordinary skill in such arts.

Figure 1:
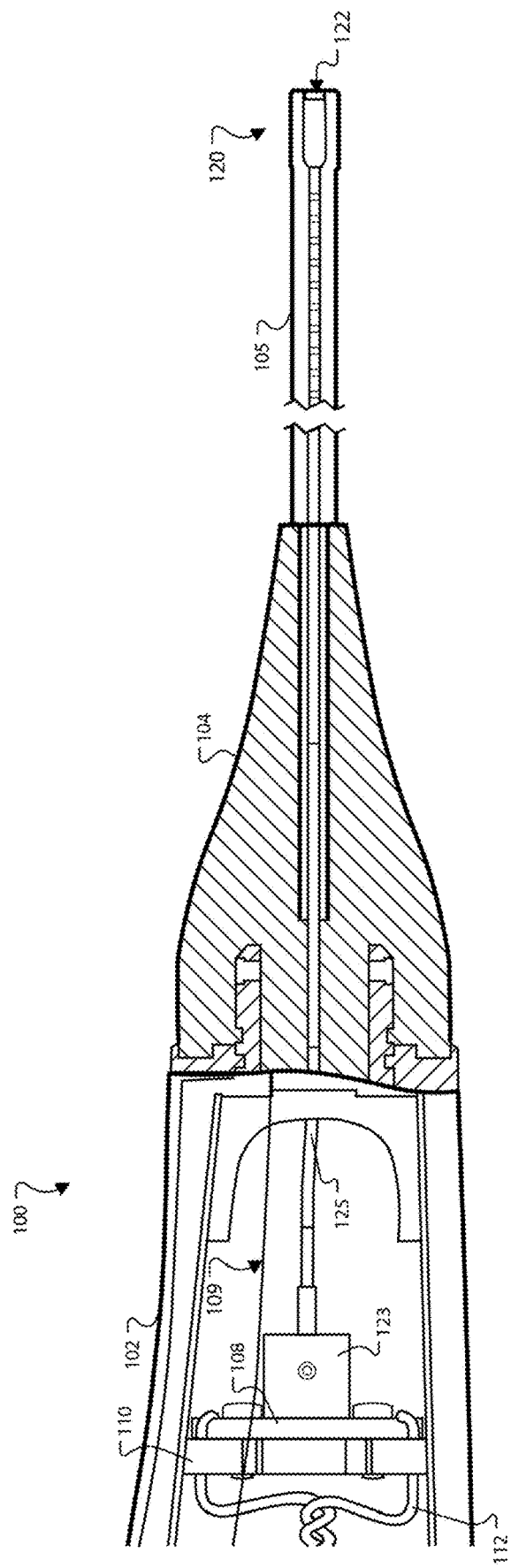
FIG. 1 is cross-sectional diagram of a laryngoscope according to an example embodiment of the invention.

FIG. 1 is cross-sectional diagram of a laryngoscope 100 according to an example embodiment of the invention, and FIGS. 2-5 show further views of the same example laryngoscope 100. In this embodiment, laryngoscope 100 is a rhino-laryngoscope including a body 102 and an articulating shaft 105. The entirety of body 102 and its components are not shown in order to avoid obscuring the inventive features of the lighting system as described herein. A flexible housing 104 is connected to body 102 and surrounds shaft 105 to offer mechanical support and stability during articulating operation. Shaft 105 articulates upward and downward (within the plane of the figure) under control of pull wires 109.

The distal tip 120 of shaft 105 includes an image sensor assembly 130 (seen in the cutaway view of FIG. 5), which includes a CMOS imaging sensor and may include various focusing optics. In other embodiments, a CCD imaging sensor or other sensor known in the art may be used. Image sensor assembly 130 receives image light through imaging lens 124 positioned centrally on distal face 122, providing the scope's camera.

The illumination system includes an enclosed LED 123 mounted to a circuit board 108, which is connected to body 102 through a mechanical support 110. Power leads 112 pass through support 110 to supply power to circuit board 108 to supply LED 123. Two pairs of fiber bundles are contained in a common ferrule 125, which is connected to the housing of enclosed LED 123 to allow the fiber bundles to pass through the housing and be coupled to LED 123 to receive light. Preferably, butt-coupling is used, in which the end of the fiber bundles is positioned near the light emitting surface of LED 123 without a lens. Other known types of coupling may be used. LED 123 has an output numerical aperture (NA) providing a critical angle larger than the field of view of the image sensor assembly 130, as will be further discussed below.

Figure 4:
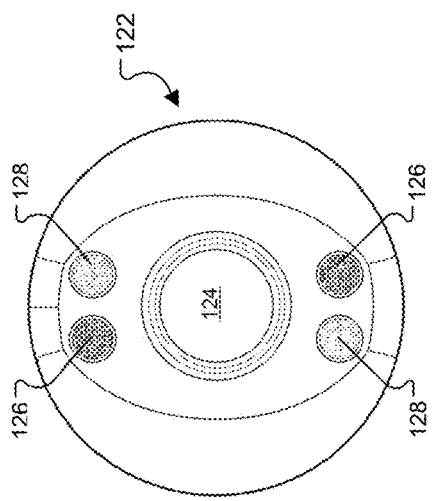
FIG. 4 is an end-on view of the shaft distal face of the laryngoscope of FIG. 1.
Figure 5:
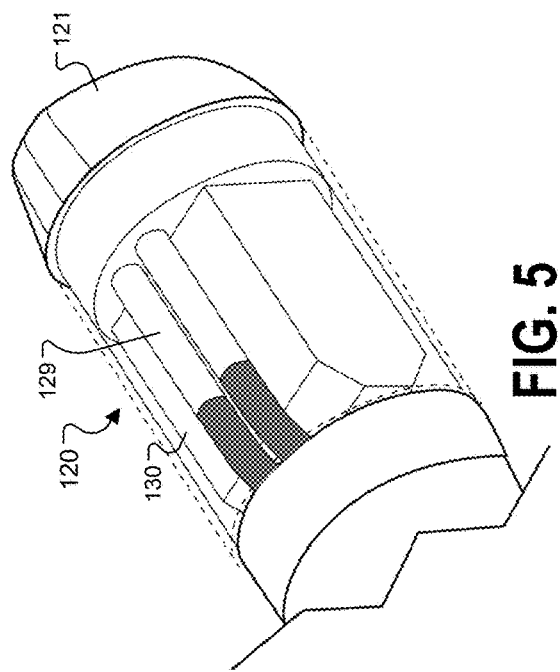
FIG. 5 is a back perspective cutaway view of the shaft distal tip of the laryngoscope of FIG. 1.
Figure 3:
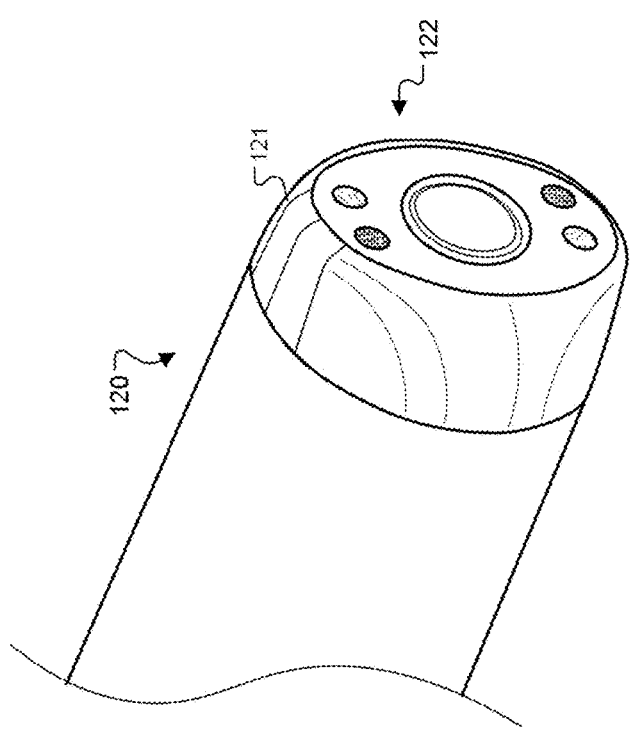
FIG. 3 is a front perspective view of the shaft distal tip of the laryngoscope of FIG. 1.

The fiber bundles include a first pair of fiber bundles 126 and a second pair of fiber bundles 128 (FIG. 2, FIG. 4). Both pairs of bundles pass through the shaft and to the distal tip 120. The distal ends preferably have no diffusion lenses and are presented at the shaft distal face 122 flush with the surface. Each fiber bundle is enclosed with a metal ferule 129 (FIG. 5) toward the distal end, which is bonded along the perimeter of openings in distal face 122 to secure the fiber bundles in place. Preferably the fiber bundles 126 and 128 are oriented perpendicular to the face at their distal ends. As seen in the end-on view of FIG. 4, in this embodiment the distal ends of two pairs of fiber bundles 126 and 128 are positioned above and below imaging lens 124 to provide illumination light. One bundle from each pair is above the lens 124, and one bundle from each pair is below. The shaft distal face 122 in this embodiment is elongated along its vertical axis, and shorter along the horizontal axis. The first pair of fiber bundles 126 are positioned opposite each other above and below the imaging lens and the second pair of fiber bundles 128 are positioned opposite each other above and below the imaging lens. In order to provide the least traumatic procedure possible for the patient, and also to make best use of the cross section of the distal end, preferably the shaft distal tip 120 is tapered toward distal face 122 at least on vertical sides of distal tip 120. The taper is formed in a distal assembly 121 which is connected to shaft 105.

The first pair of fiber bundles 126 have a numerical aperture (NA) providing a critical angle less than the field of view of imaging lens 124 and imaging sensor assembly 130. The second pair of fiber bundles having a NA providing a critical angle as large or larger than the field of view. As further discussed below, the use of high-NA and low-NA fiber bundles together, positioned around the imaging lens, creates an illumination light field with a relatively higher intensity in a central portion, a relatively lower intensity surrounding the central portion, with all of the fiber bundles contributing to create a spatially diverse light field with a circumferentially even light intensity within the field of view. While the typical field of view of a rhino-laryngoscope is around 70 to 85 degrees, the present wide-angle rhino-laryngoscope has a field of view of 100 degrees to provide imaging of more of the nasal cavity walls. This angle means that the illumination fiber needs an NA greater than 0.77 to illuminate the entire field of view. In the preferred version, a fiber that has a numerical aperture of 0.86 is used for the second pair of fiber bundles. The first pair of fiber bundles is preferably implemented with fiber that has an NA of 0.64. The use of a high-NA and low-NA fiber, together with the spatial diversity of emitters provided through having at least a pair of fiber bundles of each type at the distal face, decreases the intensity of the illumination at the edge of the field of view and helps provide an even distribution of illumination in the nasal cavity.

Figure 7:
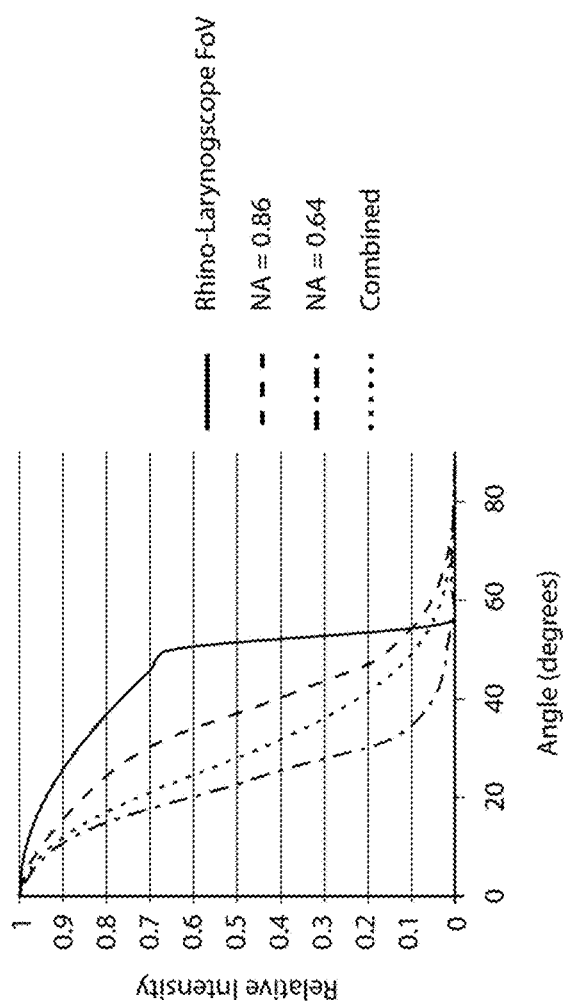
FIG. 7 shows a chart comparing light intensity of fiber bundle emissions according to some embodiments of the invention.

While these particular optic fibers are used in this embodiment, other embodiments may use other combinations of high-NA and low-NA fiber. More than two types of fiber may also be used. Generally, the type of fiber chosen for the second (high-NA) fiber will depend on the desired field of view of the scope. The high-NA should provide a critical angle greater than the field of view (as measured from a zero-degree center). The low-NA fiber should be chosen to provide a desired shape to the light field, as further described below. Precise values are not critically important in some cases. For example, with a scope having a field of view of about 100 degrees, the NA of the first pair of fiber bundles is preferably less than 0.7, and more preferably less than 0.65, and the NA of the second pair of fiber bundles is greater than 0.77. For a field of view of 110 degrees, for example, the second pair of fiber bundles should have an even higher NA The relative intensity of the output for these two different types of fiber is shown in FIG. 7, which shows a chart comparing light intensity of emitted light from the two types of fiber described above. The chart vertical axis shows normalized light intensity of emitted or received light, while the horizontal axis shows the degrees off of center at which the intensity value is obtained. As shown in the legend, the field of view for a Rhino-Laryngoscope according to one embodiment is depicted along with the emission patterns. The field of view drops off sharply around 50 degrees from center. The low-NA fiber used in this embodiment has the lowest depicted emission curve, passing about 80% at 20 degrees from center, and dropping sharply to under 10% at 40 degrees from center. The high-NA fiber employed in this embodiment can be seen has a wider field of emission, dropping to 80% around 30 degrees, and dropping below 10% at slightly over 50 degrees. The final graph in the legend shows the combined light field of the low-NA and high-NA fibers when used together.

Figure 8:
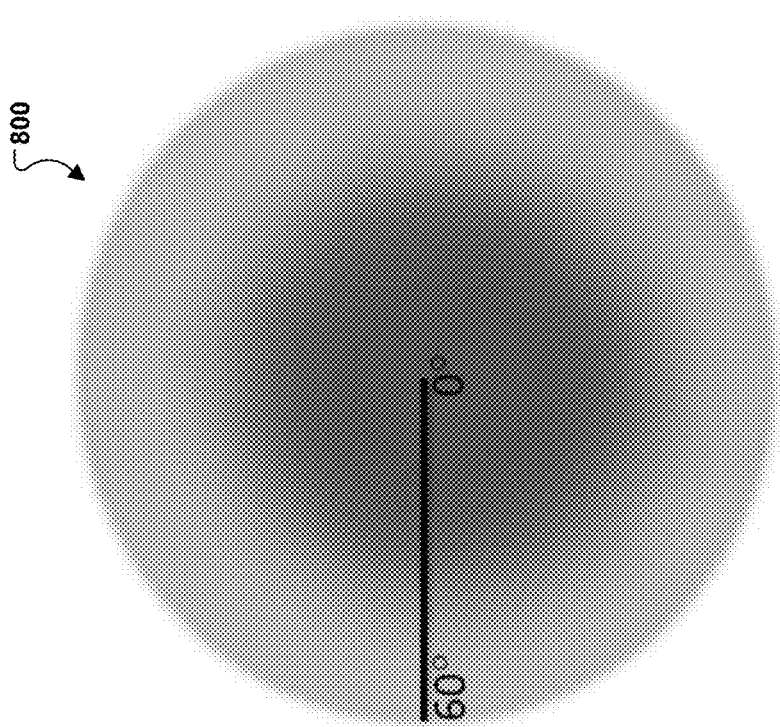
FIG. 8 shows a two-dimensional light intensity field according to some embodiments of the invention.

FIG. 8 shows a two-dimensional light intensity field 800 according to some embodiments of the invention. Light intensity field 800 is produced by the illumination system of the embodiment in FIG. 3 and FIG. 4. Generally, the depicted field 800 has an intensity as shown by the combined curve of FIG. 7. Due to the spatial diversity of the fiber bundles 126 and 128 positioned along the shaft distal face 122, a spatially diverse light field with a circumferentially even light intensity within the field of view. Generally, at least part of the field of view is illuminated with first imaging light from two or more illuminating areas, the first imaging light emitted from a first pair of fiber bundles with NAs providing a critical angle less than the field of view. The entire field of view is also illuminated with second imaging light from a second two or more illuminating areas, the second imaging light emitted from a second pair of fiber bundles with NAs providing a critical angle at or greater than the field of view.

FIG. 6a is a block diagram of a flexible endoscope system 600 according to some embodiments of the invention. System 600 includes a camera control unit (CCU) coupled to a rhino-laryngoscope 100 through a power supply and data cable 604. Only the features relevant to the illumination system are shown to simply the diagram. Generally, CCU 602 includes image processing circuitry performing digital image processing functions to process and filter the received images as is known in the art. CCU 602 may also include a display for showing imagery from rhino-laryngoscope 100, or a video output for feeding an external display. Data could also be passed wirelessly, by means known in the art, and/or power can be supplied to the unit by another means, such as an onboard battery, obviating the need for the power supply and data cable 604 in some embodiments. A further embodiment is shown in the system 650 of FIG. 6b, wherein at least the LED driver, and optionally the imaging electronics are elements of the supply cable rather than the endoscope handle element.

Rhino-laryngoscope 100 includes a CMOS imager 130, in this embodiment positioned near the shaft distal tip to receive imaging light from the subject scene. Image data is passed from CMOS imager 130 to CMOS imager electronics 630, which processes the raw image data to produce a desired video or image stream. The video or image stream is then transmitted over power supply and data cable 604 to CCU 602.

The illumination system of rhino-laryngoscope 100 includes enclosed LED 123, an LED driver 610, and pairs of high-NA fiber bundles 128 and low-NA fiber bundles 126 which pass to the distal tip of the scope to illuminate the subject scene. LED driver 610 may be located on circuit board 108 (FIG. 1) or on a main control board or module (not shown separately) for rhino-laryngoscope 100. LED driver 610 drives power to LED 123 at a desired voltage and current, which may be adjustable. Light produced by LED 123 passes to the proximal end of fiber bundles 126 and 128, which may be grouped together in a common ferrule for coupling to LED 123. Fiber bundles 126 and 128 then pass through the scope shaft and have their distal ends presented at the shaft distal face.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. An optical device for use in endoscope procedures comprising:
   a body;
   an elongated shaft connected to the body and having a distal tip with a distal face;
   an optical assembly including an imaging lens at the shaft distal face and having a field of view of at least 90 degrees, where the field of view has an angular value of $2\theta_{fov}$;
   an illumination system including:
      a light emitting diode (LED) coupled to the body, the LED having a radiation distribution larger than the field of view;
      a first pair of fiber bundles having proximal ends positioned to receive light from the LED, the first pair of fiber bundles passing through the shaft with distal ends having no diffusion lenses and presented at the shaft distal face, the first pair of fiber bundles having a first numerical aperture (NA) value with an associated critical angle $\theta_{c1}$, where $\theta_{c1} < \theta_{fov}$;
      a second pair of fiber bundles having proximal ends positioned to receive light from the LED, the second pair of fiber bundles passing through the shaft with distal ends having no diffusion lenses and presented at the shaft distal face, the second pair of fiber bundles having a second numeral aperture (NA) value with an associated second critical angle $\theta_{c2}$, where $\theta_{c2} \geq \theta_{fov}$; and
      wherein the distal ends of first and second pairs of fibers are positioned around the imaging lens such that they create a light field with a higher intensity in a central portion, a lower intensity surrounding the central portion, and all the fiber bundles contribute to create a spatially diverse light field with a circumferentially even light intensity within the field of view.

2. The optical device of claim 1 wherein the distal ends of first pair of fiber bundles are positioned opposite each other around the imaging lens.

3. The optical device of claim 1 wherein the field of view is at least 100 degrees, the first numerical aperture value of the first pair of fiber bundles is less than 0.7, and the second numerical aperture value of the second pair of fiber bundles is greater than 0.77.

4. The optical device of claim 3 wherein the field of view is at least 100 degrees, the first numerical aperture value of the first pair of fiber bundles is about 0.64, and the first numerical aperture value of the second pair of fiber bundles is about 0.86.

5. The optical device of claim 1 further comprising a plurality of additional fiber bundles with proximal ends receiving light from the LED and distal ends presented at the shaft distal face distributed around the imaging lens, each of the additional fiber bundles including some fibers with the first numerical aperture value of the first fiber bundle and some fibers with the second numerical aperture of the second fiber bundle.

6. The optical device of claim 1 wherein the first and second pairs of fiber bundles are butt-coupled to the LED at a LED assembly in the body.

7. The optical device of claim 1 wherein the shaft distal face has a horizontal and vertical axis, wherein the shaft distal face is longer along its vertical axis than its horizontal axis, and first pair of fiber bundles are positioned opposite each other above and below the imaging lens and the second pair of fiber bundles are positioned opposite each other above and below the imaging lens, wherein the regions above and below the imaging lens are on the distal face along the vertical axis.

8. The optical device of claim 7, wherein the shaft distal tip is tapered toward the distal face at least on vertical sides of the distal tip.

9. The optical device of claim 7, wherein the shaft distal tip includes an image sensor assembly positioned behind the imaging lens, the image sensor assembly extending further along the horizontal axis than the position of the fiber bundles along the vertical axis.

10. The optical device of claim 9, wherein the optical device is a laryngoscope and the spatially diverse light field has an intensity of 80%, relative to a central peak intensity, at about 22 degrees off center, and less than 30%, relative to the central peak intensity, at 40 degrees off center.

11. The optical device of claim 1 further comprising a supply cable containing a LED driver connected to the LED, the cable also transmitting collected imaging data to a camera control unit and power from the camera control unit to the optical device.

12. A method comprising:
positioning an optical scope in a body cavity with a shaft distal face directed at an area of interest, the optical scope having a field of view of at least 90 degrees, where the field of view has an angular value of $2\theta_{fov}$;
illuminating at least part of the field of view with first imaging light from two or more illuminating areas, the first imaging light emitted from a first pair of fiber bundles with a first numerical aperture (NA) value with associated first critical angle $\theta_{c1}$, where $\theta_{c1} \leq \theta_{fov}$;
illuminating the field of view with second imaging light from a second two or more illuminating areas, the second imaging light emitted from a second pair of fiber bundles with a second numerical aperture (NA) value with associated second critical angle $\theta_{c2}$ where $\theta_{c2} \geq \theta_{fov}$; and
the first and second imaging light combining to create a spatially diverse light field with a circumferentially even light intensity within the field of view.

13. The method of claim 12 wherein the field of view is at least 100 degrees, the first numerical aperture value of the first pair of fiber bundles is less than 0.7, and the second numerical aperture value of the second pair of fiber bundles is greater than 0.85.

14. The method of claim 13 wherein the field of view is at least 100 degrees, the first numerical aperture value of the first pair of fiber bundles is about 0.64, and the second numerical aperture value of the second pair of fiber bundles is about 0.86.

15. The method of claim 12, further comprising emitting one of the first or second image light from each of a plurality of additional fiber bundles with proximal ends receiving light from the LED and distal ends presented at the shaft distal face distributed around the imaging lens, the additional fiber bundles including some fibers with the first numerical aperture value of the first fiber bundle and some fibers with the second numerical aperture value of the second fiber bundle.

16. The method of claim 12, wherein the spatially diverse light field has an intensity of 80%, relative to a central peak intensity, at about 22 degrees off center, and less than 30%, relative to the central peak intensity, at 40 degrees off center.

* * * * *